(12) United States Patent
Roe et al.

(10) Patent No.: US 8,383,878 B2
(45) Date of Patent: Feb. 26, 2013

(54) ABSORBENT ARTICLE HAVING A MULTIFUNCTIONAL CONTAINMENT MEMBER

(75) Inventors: Donald Carroll Roe, West Chester, OH (US); Michael Dale Trennepohl, Cincinnati, OH (US); Olaf Erik Alexander Isele, West Chester, OH (US); Kenneth Michael Hamall, West Chester, OH (US); Angelli Sue Denmon, Hamilton, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 592 days.

(21) Appl. No.: 11/810,735

(22) Filed: Jun. 7, 2007

(65) Prior Publication Data
US 2007/0287981 A1 Dec. 13, 2007

Related U.S. Application Data

(60) Provisional application No. 60/811,700, filed on Jun. 7, 2006.

(51) Int. Cl.
*A61F 13/15* (2006.01)
*A61F 13/20* (2006.01)
(52) U.S. Cl. ............... 604/378; 604/385.01; 604/385.28
(58) Field of Classification Search .................. 604/367, 604/385.01, 378
See application file for complete search history.

(56) References Cited

U.S. PATENT DOCUMENTS

| | | |
|---|---|---|
| 1,917,979 A | 7/1933 | Kelly |
| 2,652,058 A | 9/1953 | Carpenter |
| 2,699,171 A | 1/1955 | McWilliams |
| 3,441,025 A | 4/1969 | Ralph |
| 3,635,221 A | 1/1972 | Champaigne |
| 3,658,064 A | 4/1972 | Pociluyko |
| 3,825,006 A | 7/1974 | Ralph |
| 4,116,892 A | 9/1978 | Schwarz |
| 4,834,741 A | 5/1989 | Sabee |
| 4,900,317 A | 2/1990 | Buell |
| 4,940,464 A | 7/1990 | Van Gompel et al. |
| 4,962,571 A | 10/1990 | Visser |
| 5,069,672 A | 12/1991 | Wippler et al. |
| 5,077,868 A | 1/1992 | Visser |
| 5,092,861 A | 3/1992 | Nomura et al. |

(Continued)

FOREIGN PATENT DOCUMENTS

| | | |
|---|---|---|
| EP | 0640329 A | 3/1995 |
| EP | 0 858 787 | 8/1998 |

(Continued)

OTHER PUBLICATIONS

U.S. Appl. No. 11/599,862, filed Nov. 15, 2006, Richard Lodge, et al.

(Continued)

*Primary Examiner* — Michele M Kidwell

(74) *Attorney, Agent, or Firm* — William E. Gallagher; Richard L. Alexander

(57) ABSTRACT

An absorbent article such as a diaper, training pant, and the like comprises a containment member that has a central zone and a barrier zone. The central zone has greater air flow according to the Air Permeability Test than the barrier zone. The barrier zone a greater hydrohead according to the Hydrostatic Head Pressure Test than the central zone. The containment member may be used for absorbent core formation and may have portions configured to serve as barrier leg cuffs for the finished absorbent article.

20 Claims, 8 Drawing Sheets

U.S. PATENT DOCUMENTS

| | | | |
|---|---|---|---|
| 5,143,679 A | 9/1992 | Weber et al. | |
| 5,156,793 A | 10/1992 | Buell et al. | |
| 5,167,897 A | 12/1992 | Weber et al. | |
| 5,217,447 A | 6/1993 | Gagnon | |
| 5,246,433 A | 9/1993 | Hasse et al. | |
| 5,374,262 A | 12/1994 | Keuhn et al. | |
| 5,386,595 A | 2/1995 | Kuen et al. | |
| 5,422,172 A | 6/1995 | Wu | |
| 5,518,801 A | 5/1996 | Chappell et al. | |
| 5,569,234 A | 10/1996 | Buell et al. | |
| 5,626,571 A * | 5/1997 | Young et al. | 604/370 |
| 5,635,588 A | 6/1997 | Eshuis et al. | |
| 5,643,239 A | 7/1997 | Bodford et al. | |
| 5,643,588 A | 7/1997 | Roe et al. | |
| 5,897,545 A | 4/1999 | Kline et al. | |
| 5,944,707 A | 8/1999 | Ronn | |
| 5,957,908 A | 9/1999 | Kline et al. | |
| 6,013,589 A | 1/2000 | Desmarais et al. | |
| 6,049,024 A | 4/2000 | Thomas et al. | |
| 6,120,487 A | 9/2000 | Ashton | |
| 6,120,489 A | 9/2000 | Johnson et al. | |
| 6,306,121 B1 | 10/2001 | Damaghi et al. | |
| 6,383,431 B1 | 5/2002 | Dobrin et al. | |
| 6,413,249 B1 | 7/2002 | Turi et al. | |
| 6,423,043 B1 | 7/2002 | Gustafsson | |
| 6,547,774 B2 | 4/2003 | Ono et al. | |
| 6,605,172 B1 | 8/2003 | Anderson et al. | |
| 6,632,211 B2 | 10/2003 | Otsubo | |
| 7,122,022 B2 | 10/2006 | Drevik | |
| 7,815,617 B2 | 10/2010 | Dircks et al. | |
| 7,819,849 B2 | 10/2010 | Dircks et al. | |
| 2001/0023341 A1 | 9/2001 | Karami | |
| 2001/0041879 A1 | 11/2001 | Karami et al. | |
| 2001/0042584 A1 | 11/2001 | Karami et al. | |
| 2002/0035354 A1 | 3/2002 | Mirle et al. | |
| 2002/0045879 A1 | 4/2002 | Karami | |
| 2002/0138065 A1 | 9/2002 | Yeater | |
| 2002/0151858 A1 | 10/2002 | Karami et al. | |
| 2002/0193032 A1 | 12/2002 | Newkirk | |
| 2003/0065298 A1 | 4/2003 | Krishnaswamy-Mirle et al. | |
| 2003/0078558 A1 | 4/2003 | Karami et al. | |
| 2003/0144645 A1 | 7/2003 | Karami | |
| 2003/0220626 A1 | 11/2003 | Karami | |
| 2003/0225382 A1 | 12/2003 | Tombult-Meyer et al. | |
| 2004/0082933 A1 | 4/2004 | Karami | |
| 2004/0167486 A1 | 8/2004 | Busam et al. | |
| 2004/0193134 A1 | 9/2004 | Mueller et al. | |
| 2005/0154366 A1 | 7/2005 | Karami et al. | |
| 2005/0177123 A1 | 8/2005 | Catalan | |
| 2005/0256476 A1 | 11/2005 | Mirle et al. | |
| 2006/0155253 A1 | 7/2006 | Dziezok et al. | |
| 2006/0155254 A1 | 7/2006 | Dziezok et al. | |

FOREIGN PATENT DOCUMENTS

| | | |
|---|---|---|
| GB | 243 719 | 2/1926 |
| GB | 2268389 A | 1/1994 |
| JP | 07-328067 A | 12/1995 |
| JP | 2000-300603 A | 10/2000 |
| WO | WO 97/36561 A | 10/1997 |
| WO | WO 98/48750 | 11/1998 |

OTHER PUBLICATIONS

U.S. Appl. No. 11/810,745, filed Jun. 7, 2007, Richard Lodge, et al.
U.S. Appl. No. 11/810,742, filed Jun. 7, 2007, Richard Lodge, et al.
U.S. Appl. No. 11/810,734, filed Jun. 7, 2007, Richard Lodge, et al.
U.S. Appl. No. 11/810,779, filed Jun. 7, 2007, Richard Lodge, et al.
U.S. Appl. No. 11/810,715, filed Jun. 7, 2007, Richard Lodge, et al.
U.S. Appl. No. 11/810,733, filed Jun. 7, 2007, Richard Lodge, et al.
U.S. Appl. No. 11/810,736, filed Jun. 7, 2007, Fred Desai, et al.
U.S. Appl. No. 11/810,777, filed Jun. 7, 2007, Frederick Langdon, et al.
U.S. Appl. No. 11/810,741, filed Jun. 7, 2007, Fred Desai, et al.
U.S. Appl. No. 11/810,708, filed Jun. 7, 2007, Donald C. Roe, et al.

* cited by examiner

US 8,383,878 B2

ABSORBENT ARTICLE HAVING A MULTIFUNCTIONAL CONTAINMENT MEMBER

CROSS REFERENCE TO RELATED APPLICATION

This application claims the benefit of U.S. Provisional Application No. 60/811,700, filed Jun. 7, 2006, the substance of which is incorporated herein by reference.

FIELD OF THE INVENTION

The present invention relates to absorbent articles, which are capable of absorbing bodily exudates, having a containment member with zoned characteristics which forms an integral barrier leg cuff.

BACKGROUND OF THE INVENTION

Absorbent articles such as diapers, training pants, incontinence briefs, and the like are well known for their convenience in absorbing and containing body exudates. Typical absorbent article construction involves various structures having defined properties aiding the fit or functionality of the article. However, it is advantageous to reduce the number of structures and amount of material present in absorbent articles. For disposable absorbent articles, fewer structures and less material results in reduced disposable mass. Fewer structures may also simplify the processing of the absorbent article. Fewer structures may also reduce the total cost of the absorbent article. One way to reduce the number of structures and amount of material present in an absorbent article is by combining the function of multiple structures into a single structure. The core support and the barrier leg cuff are two such structures that may be combined.

The core support is a substrate upon which the absorbent core is disposed. The core support typically comprises an air permeable material such as a nonwoven web, a cellulosic tissue, an apertured film, or other like materials. The core support may assist in maintaining the integrity of the absorbent core. In particular, the cores of modern absorbent articles comprise relatively high percentages of superabsorbent polymer (SAP) particles. Prior to liquid insult, the SAP particles often resemble grains of sand. The core support may be used to confine the SAP particles within the core and to prevent the SAP particles from becoming distributed throughout the absorbent article. Additionally, the core support may be a necessary component of core formation. The core support may serve as the formation layer upon which the components of the core are placed during the process of forming the core. Typical core components include SAP particles and cellulosic fluff. During the formation of the core, a vacuum is often drawn through the core support so that core components disposed on the core support remain immobilized. This type of vacuum formation necessitates a core support that has a relatively high degree of air permeability, an air flow measured in, for example, $m^3/m^2/min$, such that a vacuum may be drawn through the core support.

Barrier leg cuffs (e.g., also referred to as inner cuffs, inner leg cuffs, leg gussets, standing leg cuffs, barrier cuffs) are physical barriers which inhibit loose fecal material, urine, or liquids from escaping the article. The barrier cuffs restrain the free movement of exudates and provide a structure to contain the exudates within the diaper. Typical barrier cuffs include a pair of flaps disposed longitudinally on the article and running at least through the crotch region of the article. The barrier cuffs are laterally spaced so as to allow for the receipt of body exudates into the absorbent article. Barrier cuffs typically comprise an elastic member associated with the barrier cuff that allows the barrier cuff to stand up and serve as a physical barrier to exudate leakage or run-off from the body-facing surface of the article. The flaps may comprise a liquid impermeable material. Suitable liquid impermeable materials include materials that are substantially or fully liquid impermeable or may be treated to become more liquid impermeable such as woven webs, nonwoven webs, films, and other like materials. Another consideration for flap construction is breathability. During wear, a portion of the barrier leg cuff is in contact with the wearer. A barrier leg cuff having a breathable flap is desirable to prevent occlusion and over hydration of the skin. The flap may be constructed from a material that has some degree of air and vapor permeability.

Combining the core support and the barrier leg cuff into a single structure requires that the structure perform different functions at different locations in the diaper. For example, the single structure may require, in some regions, the air permeability and SAP particle retention properties of the core support and may require, in other locations, the liquid impermeability and air/vapor permeability of the barrier leg cuff. While integrating barrier leg cuffs with a substrate underlying the core has been tried in absorbent articles (e.g., U.S. Pat. No. 5,643,239), previous executions have failed to appreciate the multiple functions that the integrated structure must exhibit. Particularly, previous applications have failed to appreciate the dynamic between high air permeability in certain zones (e.g., for core formation) and liquid impermeability in other zones (e.g., for barrier protection). As a result, previous executions disclose an integrated structure that may compromise one of the functions that the structure was intended to perform (e.g., requisite air permeability versus liquid impermeability).

SUMMARY OF THE INVENTION

In light of the problems discussed above, the present invention relates to a disposable absorbent article having multifunctional containment member that forms an integral core support and barrier leg cuff. The present invention relates to an absorbent article comprising a garment body and an absorbent assembly joined to the garment body such that the absorbent assembly is disposed between the garment body and a wearer during wear. The absorbent assembly has a garment-facing surface and a body-facing surface. The absorbent assembly comprises a liquid permeable topsheet, a containment member joined to the topsheet, and an absorbent core disposed between the containment member and the topsheet. The containment member comprises opposing upstanding edges and an elastic member joined proximate to the upstanding edge such that the elastic member lifts a portion of the containment member away from the body-facing surface of absorbent assembly during wear of the absorbent article. The containment member comprises a central zone disposed between the absorbent core and the garment body and a pair of barrier zones disposed between the central zone and the opposing upstanding edges of the containment member. The central zone may have a greater air flow according to the Air Permeability Test than the barrier zone and the barrier zone may have a greater hydrohead according to the Hydrostatic Head Pressure Test than the central zone.

The present invention also relates to an absorbent article wherein the containment member comprises a central zone disposed between the absorbent core and the garment body, a bond zone disposed adjacent to the elastic member, and a barrier zones disposed between the central zone and the upstanding edge of the containment member. The central zone may have a greater air flow according to the Air Permeability Test than the barrier zone. The bond zone may have a greater hydrohead according to the Hydrostatic Head Pressure Test than the barrier zone.

BRIEF DESCRIPTION OF THE DRAWINGS

In the accompanying drawing, like reference numerals identify like elements, which may or may not be identical in the several exemplary embodiments that are depicted. Some of the figures may have been simplified by the omission of selected elements for the purpose of more clearly showing other elements. Such omissions of elements in some figures are not necessarily indicative of the presence or absence of particular elements in any of the exemplary embodiments, except as may be explicitly delineated in the corresponding written description.

DETAILED DESCRIPTION OF THE INVENTION

Figure 1:
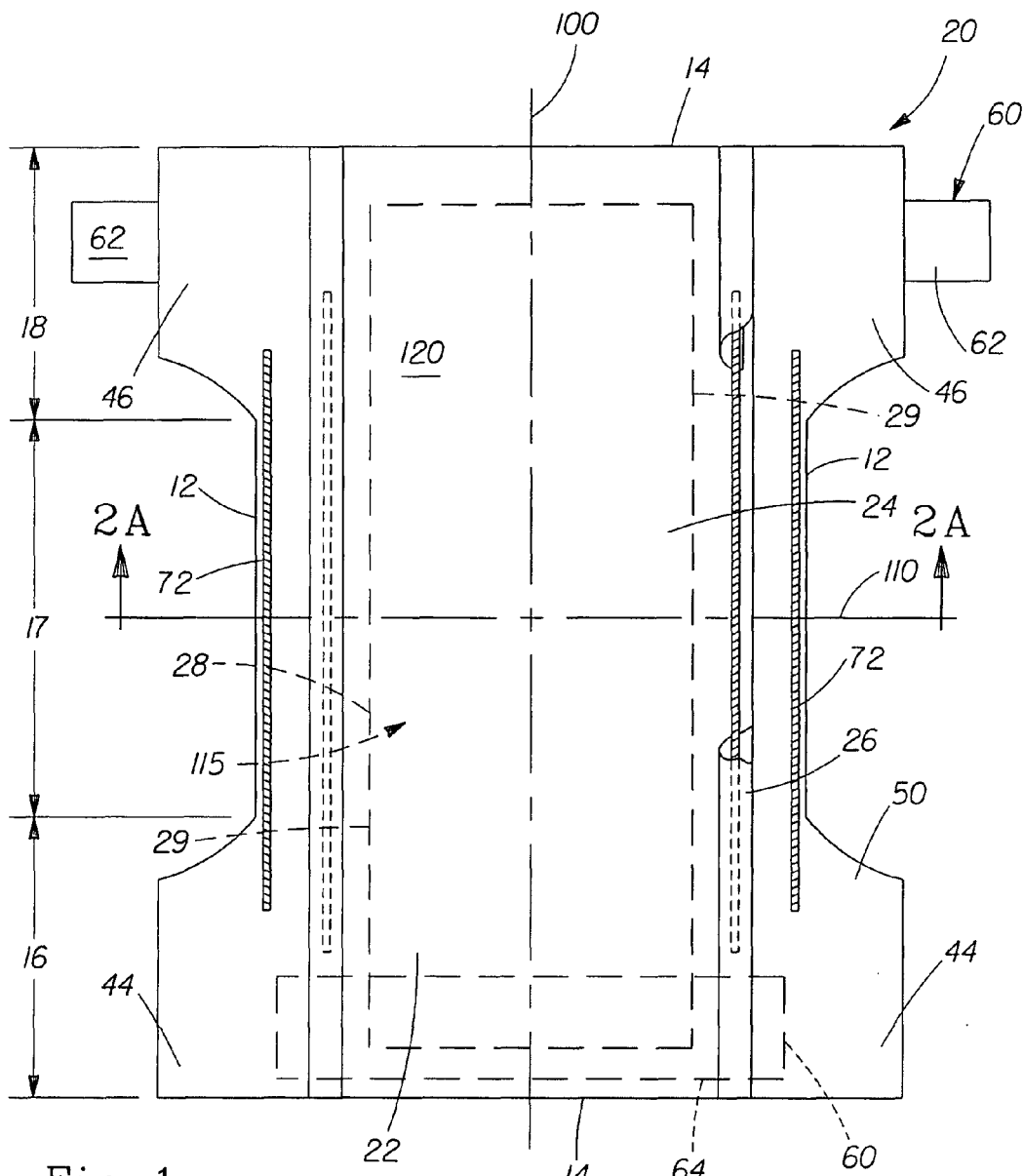
FIG. 1 is a plan view of an exemplary, non-limiting embodiment of an absorbent article in the form of a diaper.

As used herein, the following terms shall have the meaning specified thereafter:

"Disposable," in reference to absorbent articles, means that the absorbent articles are generally not intended to be laundered or otherwise restored or reused as absorbent articles (i.e., they are intended to be discarded after a single use and, preferably, to be recycled, composted or otherwise discarded in an environmentally compatible manner).

"Absorbent article" refers to devices which absorb and contain body exudates and, more specifically, refers to devices which are placed against or in proximity to the body of the wearer to absorb and contain the various exudates discharged from the body. Exemplary absorbent articles include diapers, training pants, pull-on pant-type diapers, refastenable diapers or pant-type diapers, incontinence briefs and undergarments, diaper holders and liners, feminine hygiene garments such as panty liners, absorbent inserts, and the like. Absorbent articles may be disposable or may have portions that may be restored or renewed.

"Proximal" and "Distal" refer respectively to the location of an element relatively near to or far from the longitudinal or lateral centerline of a structure.

"Body-facing" and "garment-facing" refer respectively to the relative location of a structure or a surface of the structure. "Body-facing" implies the structure or surface of the structure is nearer to the wearer during wear than some other element or surface. "Garment-facing" implies the structure or surface of the structure is more remote from the wearer during wear than some other structure or surface (i.e., structure or surface is proximate to the wearer's garments that may be worn over the disposable absorbent article).

"Longitudinal" refers to a direction running substantially perpendicular from a waist edge to an opposing waist edge of the article and generally parallel to the maximum linear dimension of the article. Directions within 45 degrees of the longitudinal direction are considered to be "longitudinal"

"Lateral" refers to a direction running from a longitudinal edge to an opposing longitudinal edge of the article and generally at a right angle to the longitudinal direction. Directions within 45 degrees of the lateral direction are considered to be "lateral."

"Longitudinal Centerline" refers to a longitudinal line that can be drawn through the middle of an absorbent article. For most absorbent articles, the longitudinal centerline separates the article into two substantially symmetrical halves that will fall on the left and right halves of a wearer during wear.

"Lateral Centerline" refers to a lateral line drawn through the midpoint of the longitudinal centerline and perpendicular to the longitudinal centerline.

"Disposed" refers to an element being located in a particular place or position.

"Joined" refers to configurations whereby an element is directly secured to another element by affixing the element directly to the other element and to configurations whereby an element is indirectly secured to another element by affixing the element to intermediate member(s) which in turn are affixed to the other element.

"Extendibility" and "extensible" mean that the width or length of the component can be extended or increased from a relaxed state.

"Elastic," "elastomer," and "elastomeric" refer to a material which generally is able to extend 50% without breaking or rupturing, and is able to recover substantially to its original dimensions after the deforming force has been removed.

"Elastomeric material" is a material exhibiting elastic properties. Elastomeric materials may include elastomeric films, scrims, nonwovens, and other sheet-like structures.

"Fine fiber" is a fiber having a denier of less than about 0.1 denier. Fine fibers may be formed by conventions means including meltblowing, electro-spinning, melt-film fibrillation, and bi- or multi-component fiber splitting. It should be recognized that any recitation of a fiber formed by meltblowing, electro-spinning, melt-film fibrillation, or fiber splitting may be read to include fine fibers created by other formation techniques.

"Outboard" and "inboard" refer respectively to the location of an element disposed relatively far from or near to the longitudinal centerline of the diaper with respect to a second element. For example, if element A is outboard of element B, then element A is farther from the longitudinal centerline than is element B.

"Pant" or "Pants" refers to an absorbent article having a pre-formed waist and leg openings. A pant may be donned by inserting a wearer's legs into the leg openings and sliding the pant into position about the wearer's lower torso. Pants are also commonly referred to as "closed diapers," "prefastened diapers," "pull-on diapers," "training pants," and "diaper-pants."

"Pore size" refers to the mean flow pore size as measured according to ASTM method E-1294-89 (1999) entitled "Standard Test Method for Pore Size Characteristics of Membrane Filters Using Automated Liquid Porosimeter."

"Garment body" refers to the structure of an absorbent article that encircles the waist and legs of a wearer and maintains the position of the absorbent assembly while the absorbent article is in use on a wearer. The garment body may also serve the function of a traditional undergarment by providing coverage of the genitals, the buttocks, and a portion of the hips. In the absorbent article, the garment body is positioned such that the absorbent assembly is disposed between the garment body and the wearer during normal wear.

"Continuous substrate," when used in reference to a containment member, means a seamless substrate (i.e., a whole material as compared to a material formed by joining, placing, or seaming together discrete pieces).

"Laminated structure" or "laminate" means a structure in which one layer, material, component, web, or substrate is adhesively bonded or fused, at least in part, to another layer, material, component, web, or substrate.

"Liquid permeable" and "liquid impermeable" refer to the penetrability of materials in the context of the intended usage of disposable absorbent articles. Specifically, the term "liquid permeable" refers to a layer or a layered structure having pores, openings, and/or interconnected void spaces that permit liquid water to pass through its thickness in the absence of a forcing pressure. Conversely, the term "liquid impermeable" refers to a layer or a layered structure through the thickness of which liquid water cannot pass in the absence of a forcing pressure. Liquid impermeable materials exhibit a hydrohead of at least about 5 mbar as measured according to the Hydrostatic Head (Hydrohead) Pressure Test provided below in the Test Methods. However, it may be desirable that a liquid impermeable material exhibit a hydrohead of at least about 10 mbar or about 15 mbar. A layer or a layered structure that is water-impermeable according to this definition may be permeable to vapor (i.e., may be "vapor permeable"). Such a vapor permeable layer or layered structure is commonly known in the art as "breathable."

"Fiber" refers to a unit of matter, synthetic or natural, characterized by a high ratio of length-to-width. "Filament" refers to a fiber of indefinite length FIG. 1 is a plan view of an exemplary, non-limiting embodiment of an absorbent article of the present invention in the form of a diaper 20. The diaper 20 is shown in a flat, uncontracted state (i.e., without elastic induced contraction). The body-facing surface 120 of the diaper 20 is facing the viewer and the garment-facing surface 115 is away from the viewer. The diaper 20 includes a longitudinal centerline 100 and a lateral centerline 110. The diaper 20 is shown to have a front waist region 16, a rear waist region 18 opposed to the front waist region 16, and a crotch region 17 located between the front waist region 16 and the rear waist region 18. The diaper 20 is defined by longitudinal side edges 12 and lateral end edges 14 (which may be referred to as the waist edge). The diaper 20 may have opposing longitudinal side edges 12 that are oriented generally parallel to the longitudinal centerline 100. However, for better fit, longitudinal side edges 12 may be curved or angled to produce, for example, an "hourglass" shape diaper when viewed in a plan view. The diaper 20 may have opposing end edges 14 that are oriented generally parallel to the lateral centerline 110; however the end edges 14 may be curved or angled to provide a more contoured diaper 20.

The diaper 20 may comprise an absorbent assembly 22 joined to a garment body 50. The absorbent assembly 22 is disposed on the body-facing surface of the garment body 50. During wearer, the absorbent assembly 22 is disposed between the garment body 50 and the wearer. The absorbent assembly 22 may be joined to the garment body 50 via any means known in the art. The absorbent assembly 22 may be attached to the garment body 50 over substantially the entire garment-facing surface, or only selected regions thereof. The attachments may be substantially permanent, i.e., bonds such as adhesive bonds, or may be releasably attached, i.e., via fasteners. Various other elements are known in the art and may be included in the construction of diaper 20 to improve the fit and/or functionality.

The garment body 50 is the portion of the diaper 20 that encircles the waist and legs of a wearer. The garment body 50 serves to maintain the position of the diaper 20 while in use on a wearer. The garment body 50 also serves the function of a traditional undergarment by providing coverage of the genitals, the buttocks, and a portion of the hips.

The garment body 50 may comprise a variety of suitable substrates including woven webs, nonwoven webs, polymeric films, and combinations thereof. In certain embodiments, it may be desirable that the garment body 50 comprise a substrate that is substantially liquid impermeable so that the garment body 50 may provide a containment function. Suitable liquid impermeable materials may include certain nonwovens formed to exhibit water impermeability such as nonwovens having a requisite amount of fine fibers. Suitable liquid impermeable materials also include polymeric films, microporous films, nonwoven treated to be liquid impermeable, and other impermeable materials known in the art.

In certain embodiments, the garment body 50 need not serve a containment function, and, as a result, the garment body 50 may comprise liquid permeable materials. In certain embodiments, the garment body 50 may consist essentially of a liquid permeable material (i.e., while other liquid impermeable materials may be present in the garment body 20, these materials do not substantially affect the overall permeability of the garment body 20). Any suitable liquid permeable materials may be used. In particular, nonwoven and woven fibrous webs are generally desirable for their soft, skin-pleasing character. The webs may comprise natural and/or synthetic fibers or filaments.

In certain embodiments portions of the garment body may be or may be rendered extensible or elastic in at least one direction. Suitable materials include elastic nonwovens, elastic nonwovens laminated with extensible or elastic films or scrims, extensible nonwovens laminated with elastic films or scrims, elastomer patterns printed on elastic or extensible nonwovens, mechanically pre-strained variants of any of the preceding materials, or any other elastic or extensible materials as known in the art. Exemplary embodiments of articles incorporating extensible or elastic garment body materials, including biaxially stretchable materials, are described in copending application Ser. No. 60/811,580 entitled "Absorbent Article Having an Anchored Core Assembly" filed Jun. 7, 2006 in the name of Lodge et al.

As shown in FIG. 1, the garment body 50 may comprise a fastening system 60. When engaged, the fastening system 60 interconnects the front waist region 16 and the rear waist region 18 to form a circumscribing waist opening and two circumscribing leg openings. The fastening system 60 may comprise an engaging member 62 and a receiving member 64. The engaging member 62 may comprise hooks, loops, an adhesive, a cohesive, a tab, or other fastening mechanism. The receiving member 64 may comprise hooks, loops, a slot, an adhesive, a cohesive, or other fastening mechanism that can receive the engaging member 62. Suitable engaging member 62 and receiving member 64 combinations are well known in the art and include but are not limited to hooks/loop, hooks/hooks, adhesive/polymeric film, cohesive/cohesive, adhesive/adhesive, tab/slot, and button/button hole.

The garment body 50 may comprise one or more leg elastic members 72. The leg elastic members 72 are generally disposed adjacent the longitudinal side edges 12 proximate to the leg openings. The leg elastic members 72 may gather and hold the garment body 50 against the legs of the wearer. The leg elastic members 72 may aid in positioning the diaper 20 as well as improve the aesthetics of the diaper (e.g., diaper appears more like traditional underwear). In embodiments where the garment body 50 is substantially liquid impermeable, the leg elastic members 72 may serve a gasketing function preventing body exudates from leaking out of the diaper 20. Examples of suitable elastic members 72 include elastomeric films, elastomeric foams such as polyurethane foams or crosslinked natural rubber foams; formed elastic scrim; elastomeric films such as heat shrinkable elastic materials; elastomeric film laminates such as a laminate of a heat-shrinkable elastomeric film and a resilient member; and elastic strands made from rubber, synthetic rubber, elastomeric polyurethane, or other materials.

The garment body 50 may include front side panels 44 and back side panels 46. In certain embodiments, the front and/or back side panels 44, 46 may be unitary elements of the garment body 50 (i.e., the side panels are not separately manipulative elements secured to the garment body 50, but rather are an integral extension from the garment body 50). The garment body 50 for FIG. 1 includes unitary front and back side panels 44, 46. In certain embodiments, the front and/or side panels may be discrete elements that are joined to the garment body 50. Discrete front and/or back side panels may be joined to the absorbent assembly 22 by any bonding method known in the art. The front and back side panels may be extensible, inextensible, elastic, or inelastic. The front and back side panels may be formed from any nonwoven webs, woven webs, knitted fabrics, polymeric and elastomeric films, apertured films, sponges, foams, scrims, and combinations and laminates thereof. In certain embodiments the front and back side panels 42, 44 may be formed of a nonwoven/elastomeric material laminate or a nonwoven/elastomeric material/nonwoven laminate. In other embodiments, the side panel 44, 46 may be permanently or refastenably joined to form the pant. A suitable elastic side panel may be formed of a laminate comprising an elastomeric film (such as supplier code X25007 from Tredegar Corp, Richmond, Va.) disposed between two nonwoven layers (such as supplier code FPN332 from BBA Fiberweb, Brentwood, Tenn.).

In alternative embodiments, the garment body 50 may be preformed (i.e., pre-formed waist and leg openings) by the manufacturer to create a pant. A pant may be preformed by any suitable technique including, but not limited to, joining together portions of the article using refastenable and/or non-refastenable bonds (e.g., seam, weld, adhesive, cohesive bond, fastener, etc.). In certain embodiments, the garment body 50 may be manufactured with the fastening system 60 engaged (i.e., the engaging member 52 is joined to the receiving member 54). Suitable pants are disclosed in U.S. Pat. Nos. 5,246,433; 5,569,234; 6,120,487; 6,120,489; 4,940,464; 5,092,861; 5,897,545; and 5,957,908.

Figure 2A:
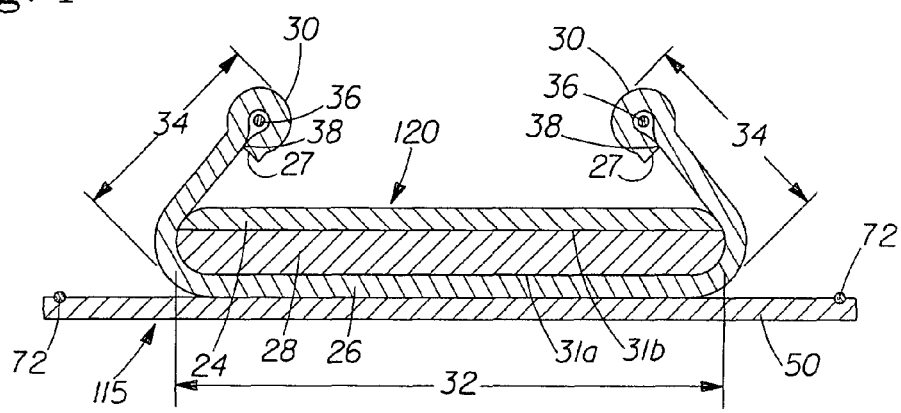
FIG. 2A is a cross-sectional view, taken along the lateral centerline, of the diaper of FIG. 1 showing a central zone and barrier zones.

The absorbent assembly 22 is the portion of the diaper 20 providing much of the absorptive and containment function. The absorbent assembly 22 comprises at least a liquid permeable topsheet 24, a containment member 26, and an absorbent core 28 disposed between the topsheet 24 and the containment member 26. It should be recognized that other structures, elements, or substrates may be positioned between the topsheet 24, core 28, and/or containment member 26. As will be discussed below, suitable optional structures include, but are not limited to, an acquisition layer, a distribution layer, a core wrap, or an impermeable member. Reference may be made to FIG. 2A for the following discussion on absorbent assembly 22 construction. FIG. 2A is a cross sectional view of the diaper of FIG. 1 taken along the lateral centerline.

The topsheet 24 is generally a portion of the diaper 20 that may be positioned at least in partial contact or close proximity to a wearer. Suitable topsheets 24 may be manufactured from a wide range of materials, such as porous foams; reticulated foams; apertured plastic films; or woven or nonwoven webs of natural fibers (e.g., wood or cotton fibers), synthetic fibers (e.g., polyester or polypropylene fibers), or a combination of natural and synthetic fibers. The topsheet 24 is generally supple, soft feeling, and non-irritating to a wearer's skin. In certain embodiments, at least a portion of the topsheet 24 is liquid pervious, permitting liquid to readily penetrate through the thickness of the topsheet 24. A particularly preferred topsheet 24 is available from BBA Fiberweb, Brentwood, Tenn. as supplier code 055SLPV09U.

In certain embodiments, the topsheet 24 may be laterally bounded by the containment member 26. As will be discussed below, the containment member 26 comprises upstanding barrier zones 34. The topsheet 24 may be disposed laterally between the barrier zones 34.

The topsheet 24 may be joined, by any means known in the art, to the absorbent core 28 and/or the containment member 26. In certain embodiments, the topsheet 24 and the containment member 26 are joined by adhesive along the periphery of the absorbent core 28; this periphery attachment may serve to encapsulate the absorbent core 28.

The absorbent core 28 has opposing longitudinal edges 29 that are oriented generally parallel to the longitudinal centerline 100. However, the longitudinal edges 29 of the absorbent core 28 may be curved or angled to produce an "hourglass" shape when viewed in a plan view. The absorbent core 28 has a garment-facing surface 31a and a body-facing surface 31b. The absorbent core 28 may comprise a wide variety of liquid-absorbent materials commonly used in disposable diapers and other absorbent articles. Examples of suitable absorbent materials include comminuted wood pulp (e.g., air felt creped cellulose wadding); melt blown polymers including co-form; chemically stiffened, modified or cross-linked cellulosic fibers; wraps and tissue laminates; absorbent foams; absorbent sponges; superabsorbent polymers; absorbent gelling materials; or any other known absorbent material or combinations of materials. The absorbent core 28 may comprise a fluid acquisition component which acquires fluid exudates and partitions the exudates away from a wearer's body, a fluid distribution component which distributes/redistributes fluid exudates points away from the point of initial exudate loading, and/or a fluid storage component which retains a majority of the fluid exudates on a weight basis. A suitable absorbent core 28 comprising an acquisition layer, a distribution layer, and/or a storage layer is described in U.S. Pat. No. 6,013,589. Other exemplary absorbent core configurations are discussed in U.S. Patent Application Publication No. 2003/0225382A1; U.S. application Ser. No. 11/329,797, entitled, "End Seal For an Absorbent Core", filed on Jan. 11, 2006; and U.S. application Ser. No. 11/329,796, entitled, "Sealed Core For An Absorbent Article", filed on Jan. 11, 2006.

In certain embodiments, the absorbent core 28 may comprise a core wrap. The core wrap at least partially covers the liquid absorbent material of the absorbent core 28, but may fully encapsulate the liquid absorbent material of the absorbent core 28. Typically, the core wrap is disposed on at least the body-facing surface of the absorbent core 28 between the topsheet 24 and the core 28. The core wrap may be useful in immobilizing the liquid absorbent material of the absorbent core 28. The core wrap may comprise a liquid pervious substrate such as a tissue or nonwoven web.

Another suitable absorbent core construction is described in U.S. Publication No. 2004/0167486 to Busam et al. The absorbent core of the aforementioned publication uses no or minimal amounts of absorbent fibrous material within the core. Generally, the absorbent core may include no more than about 20% weight percent of absorbent fibrous material (i.e., [weight of fibrous material/total weight of the absorbent core]×100).

The containment member 26 is disposed, at least in part, adjacent to the garment-facing surface of the absorbent core 28. The containment member has opposing longitudinal terminal edges 27. The containment member 26 may bend inwardly away from the body-facing surface of the diaper 20 and toward the wearer. The inward bend may be along the longitudinal edge 29 of the core 28 or may be outboard of the longitudinal edge 29 of the core 28. The containment member 26 extends to an upstanding edge 30. In certain embodiments, the upstanding edge 30 and terminal edge 27 may be coterminous. In certain embodiments, an elastic member 36 may be disposed along the containment member 26 proximate to the upstanding edge 30. The elastic member 36 may be joined to the containment member 26 continuously or discontinuously along the length of the elastic member 36. During wear, the elastic member 36 allows a portion of the containment member 26 (including a portion of the upstanding edge 30) to lift away from the body-facing surface 120 of the diaper 20 and toward the skin of a wearer. In certain embodiments, the containment member 26 may be folded over the elastic member 36 and onto itself and so as to encircle the elastic member 36. The containment member 26 may joined to itself at a bond site 38 to encapsulate the elastic member 36.

In other embodiments, the containment member 26 may be constructed to have an elasticized region such as by having elastic filaments embedded or woven in the containment member 26.

Examples of suitable elastic members 36 include elastomeric films, elastomeric foams such as polyurethane foams or crosslinked natural rubber foams; formed elastic scrim; elastomeric films such as heat shrinkable elastic materials; elastomeric film laminates such as a laminate of a heat-shrinkable elastomeric film and a resilient member; and elastic strands made from rubber, synthetic rubber, elastomeric polyurethane, or other elastic materials.

Figure 2B:
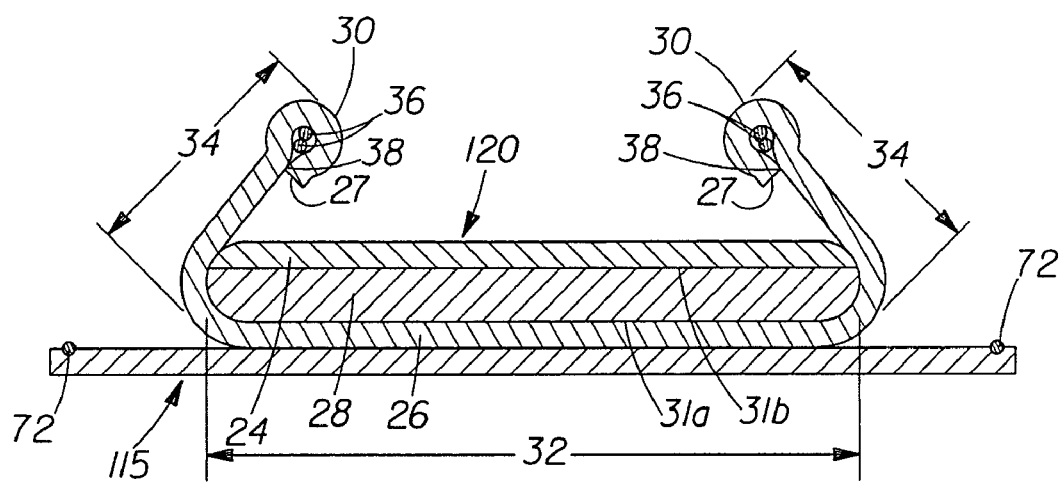
FIGS. 2B-C are alternate embodiments of the cross-sectional view as shown in FIG. 2A.
Figure 2C:
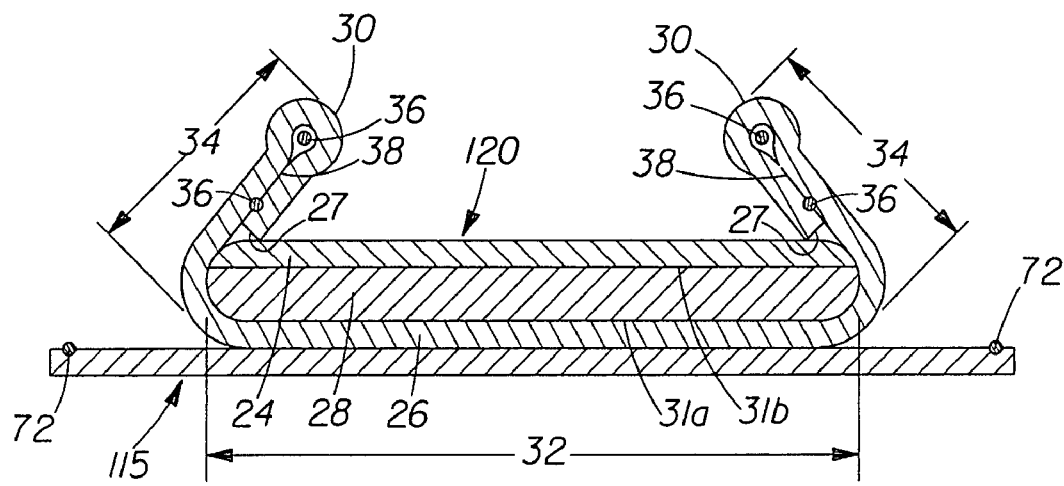

The containment member 26 may comprise multiple elastic members 36. When multiple elastic members 36 are present, the elastic members 36 may be disposed proximate to each other such as shown in FIG. 2B. In an alternate embodiment, multiple elastic members 36 may be disposed in a spaced relation such as shown in FIG. 2C (e.g., one elastic member disposed along the upstanding edge 30 and one member disposed remotely from the upstanding edge 30).

The containment member 26 may comprise a central zone 32 and a pair of barrier zones 34. The central zone 32 is a portion of the containment member 26 disposed adjacent (but not necessarily in face-to-face contact) to the garment-facing surface of the absorbent core 28. In some embodiments, the longitudinal boundary of the central zone 32 is coterminous with the longitudinal edges 29 of the absorbent core 28. However, in other embodiments, the longitudinal boundary of the central zone 32 may be inboard or outboard of the longitudinal edges 29 of the absorbent core 28. The barrier zone 34 is a portion of the containment member 26 disposed between the central zone 32 and the upstanding edge 30. The barrier zones 34 serve as barrier leg cuffs for the absorbent assembly 22. The barrier zone 34 provides a physical barrier to the free flow of exudates and provides a structure to contain the exudates within the absorbent assembly 22.

The containment member 26 may comprise a woven web, a nonwoven web, an apertured film, and a composite or laminate of any of the aforementioned materials. The containment member 26 may comprise a nonwoven, fibrous web that comprises synthetic and/or natural fibers. Suitable materials for use in a containment member 26 include a spunbond/meltblown/meltblown/spunbond (SMMS) composite materials available under supplier code MD3000 from BBA Fiberweb, Simpsonville, S.C.; SMMS composite materials available under supplier codes SM1700 and W5030 from Polymer Group, Inc., North Charleston, S.C.; a SMS composite available under supplier code B3033 from Polymer Group, Inc.; and a SMS composite available under supplier codes SM1703, SM1503, and SM1305 from First Quality Nonwovens, Inc., Great Neck, N.Y.

As discussed above, the central zone 32 and the barrier zones 34 of the containment member 26 may exhibit distinctly different physical characteristics. The central zone 32 may exhibit high air permeability for absorbent core 28 formation. In certain embodiments, the central zone 32 may exhibit an air permeability of about 100 to 300 $m^3/m^2/min$ at a pressure drop of 125 Pa, preferably around 120 to 200 $m^3/m^2/min$, as measured according to the Air Permeability Test provided below. Conversely, it is desirable that the barrier zone 34 be liquid impermeable; however, it is believed that the degree of air permeability required in the central zone would harm liquid impermeability. Therefore, the barrier zone 34 may exhibit an air permeability less than that of the central zone 32. In certain embodiments, the barrier zone 34 exhibits an air permeability that is about 10%, about 20%, about 50%, about 75%, or about 100% less than the air permeability of the central zone 32.

The barrier zone 34 may exhibit liquid impermeability for barrier protection while maintaining air and vapor permeability for wearer comfort. In certain embodiments, the barrier zone 34 exhibits a hydrohead, as measured according to the Hydrostatic Head (Hydrohead) Pressure Test provided below, of greater than about 10 mbar, 20 mbar, and 40 mbar.

Figure 3:
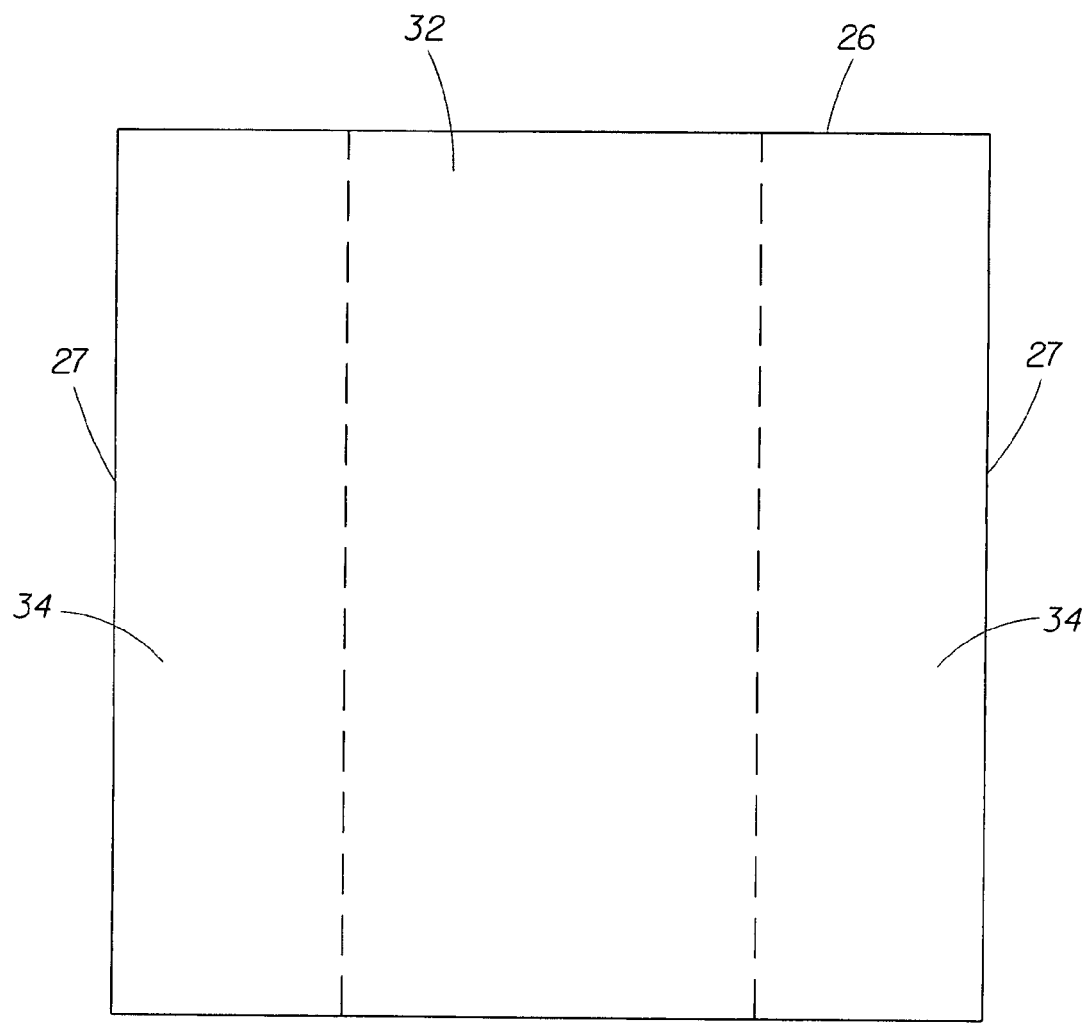
FIG. 3 is a plan view of a containment member such as provided in FIG. 2A absent other structures prior to being incorporated in a diaper.

FIG. 3 depicts a plan view of a containment member 26 without elastic members 36 and prior to being incorporated in a diaper such as shown in FIG. 1. The containment member 26 is shown having the central zone 32 and two barrier zones 34. The dotted lines represent the approximate boundary between the central zone 32 and the barrier zones 34. While this embodiment depicts the boundary between the central zone 32 and the barrier zones 34 as being linear, the boundary is not limited to straight lines. The boundary may be curvilinear or composed of connecting line segments. In certain embodiments, the boundary may be coterminous with the longitudinal edge 29 of the core 28. The disparate characteristics of the central zone 32 and the barrier zones 34 may be achieved in a variety of ways.

In one embodiment, the containment member 26 may be composed of a first discrete material that comprises the central zone 32 and a second discrete material that comprises the barrier zones 34. The first discrete material may be a porous nonwoven, an apertured film, or any other suitable substrate that permits bulk air flow yet can retain or support particulate and/or fibrous absorbent material. The second discrete material may be a liquid impermeable nonwoven such as a substantially liquid impermeable nonwoven as known in the art.

Additionally, the second discrete material may comprise a microporous film. The second discrete material may be a woven or nonwoven treated to be liquid impermeable. The first discrete material may be joined to the second discrete material by a bonding method well known in the art such as by adhesives; fusion bonding such as by heat, pressure, or ultrasonic waves; and the like. It should be recognized that the first and second materials may overlap each other in the regions where they are bonded together.

In the embodiments that follow, the containment member 26 may comprise a continuous substrate that forms the central zone 32 and the barrier zones 34. The continuous substrate may be formed, modified, or treated to yield zoned properties.

In one embodiment, the containment member 26 may be formed with laminated or composite regions that provide zoned properties. For example, the containment member 26 may comprise a spunbond/meltblown/spunbond (SMS) composite in the barrier zones 34 while the spunbond layers extend into and form the central zone 32 such that no fine fibers or a lower basis weight of fine fibers than are present in the barrier zones 34. In another example, the containment member 26 may comprise a nonwoven web having a secondary substrate (e.g., a polymeric film or other liquid impermeable material) laminated in the barrier zones 34. The secondary substrate may be joined to the nonwoven using conventional bonding means such as an adhesive or fusion bonding. The secondary substrate may be air and vapor impermeable or permeable. In one particular execution, the containment member 26 may comprise a spunbond web having a basis weight of approximately 10 gsm. The barrier zones 34 may further comprise strips of an SMS composite web adhesively joined to the spunbond web.

In another embodiment, the containment member 26 may be constructed with varying pore sizes in the central zone 32 versus the barrier zone 34. The containment member 26 may be constructed such that the central zone 32 comprises pores with a larger average size than those of the barrier zones 34. The containment member 26 may be formed with an increased basis weight of fine fibers in the barrier zones by depositing fine fibers only in those zones during the nonwoven formation process (e.g., only have meltblown heads active in those regions of the nonwoven formation beam).

In particular embodiments, the central zone 32 may comprise pores having an average pore size of about 35 to about 50 microns or, alternately, of about 40 to about 45 microns. The barrier zone 34 may comprise pores having an average pore size of about 1 to about 30 microns. However, in some executions, the barrier zone 34 may be substantially pore-free.

In certain embodiments, the containment member comprises a substrate having pores in the central zone having a first average pore size and having pores in the barrier zone having a second average pore size. The first average pore size may be about 20%, 50%, 75%, or, alternately, 100% greater than the second average pore size.

Construction of a substrate having variable pore size may be performed by any of the substrate formation (e.g., basis weight or denier modification) or substrate deformation (e.g., mechanical deformation) techniques discussed below. For example, a microporous web may be formed by stretching a polymeric film containing a pore forming agent (e.g., calcium carbonate or other relatively inert inorganic particulate material). As the film is stretched, the film separates from the pore forming agents thereby creating micropores. The size of these pores can be controlled to some extent by the degree of extension applied to the film. As a result, with increased elongation, larger pores may be formed in the central zone 32 of the containment member 26. Further discussion of microporous film formation is provided in U.S. Pat. No. 6,605,172.

In another embodiment, the relative degree of air permeability and liquid permeability may be controlled by adjusting the basis weight of the material comprising the respective zones. Particularly for nonwoven materials, decreased basis weight results in increased air permeability and water permeability. A containment member 26 constructed from a nonwoven may have a zoned basis weight such that the basis weight of the central zone 32 is less than the basis weight of the barrier zone 34. A zoned basis weight nonwoven may be formed by conventional lay-down techniques including spun-bonding, meltblowing, carding, and air laying. In one suitable execution, a nonwoven web with zoned basis weight can be formed by selectively blocking apertures of the spunbond die or by deflecting the lay-down of the formed filaments. In another suitable execution, a composite SMS nonwoven web may be formed such that the basis weight of the meltblown layer varies from the central zone 32 to the barrier zone 34. For example, a SMS web may be formed such that each of the outer layers comprise about 5-6 gsm of spunbond filaments and the inner layer comprises about 0-1.5 gsm of meltblown fibers in the central zone versus about 1-5 gsm of meltblown fibers in the barrier zone. In another suitable execution, the collector belt (i.e., the web upon which nonwoven webs such as spunbond and meltblown web may be formed) may comprise zones of higher permeability and lower permeability which may result in a web having higher basis weight and lower basis weight, respectively. Alternately, the collector belt may be subjected to varying degrees of vacuum with high vacuum areas (i.e., greater suction) resulting in higher basis weights.

In other embodiments, the relative degree of air permeability and liquid permeability may be controlled by adjusting the denier of the fibers and/or filaments used to construct the containment member 26. It is generally recognized that, given equal basis weights, a nonwoven web comprised of larger denier fibers or filaments will be more air and liquid permeable than a nonwoven web comprised of smaller denier fibers. A containment member 26 constructed from a nonwoven may have a zoned denier such that the denier of the fibers and/or filaments of the central zone 32 is greater than the denier of the fibers and/or filaments of the barrier zone 34. As a result, the central zone 32 may exhibit greater air permeability compared to the barrier zone 34, and the barrier zone 34 may exhibit greater liquid impermeability compared to the central zone 32. The preceding paragraph, describes a suitable embodiment of a nonwoven web having fine fibers in the barrier zone 34 and little to no fine fibers in the central zone 32 (e.g., SMS composite with meltblown fibers present in the barrier zone 34 but not in the central zone 32). Fiber denier may also be tailored by using splittable multi-component fibers (which include bicomponent fibers). The multi-component fibers may be spun with a particular geometry (e.g., segmented pie, hollow segmented pie, tipped trilobal, or striated) that facilitates division of the fiber into smaller subfibers upon application of an activator (e.g., mechanical energy, humidity, etc.). The multi-component fibers may be spun with a particular geometry such as an islands-in-the-sea configuration such that subfibers (e.g., islands) are created upon removal of the encasing component (e.g., sea) by means known in the art. In certain embodiments, the denier of the fibers comprising the central zone 32 and the barrier zone 34 may differ by more than about 20%, 50%, 100%, 250%, or 500%.

In other embodiments, the relative degree of air permeability and liquid permeability may be controlled by adjusting the cross-sectional shape of the fibers and/or filaments used to construct the containment member 26. Fibers that do not have a substantially round cross-sectional shape (e.g., trilobal, delta, bilobal, etc.) create more air drag. As a result, a web comprising substantially non-round fibers may have reduced air permeability compared to a web of equal denier and basis weight comprising round fibers. In a suitable embodiment, a nonwoven web may be constructed with one zone comprising predominately (greater than 50% based on number of filaments) round (e.g., circular or elliptical) cross-sectional shaped filaments and with another zone comprising predominately (greater than 50% based on number of filaments) non-round (e.g., trilobal, bilobal, delta, etc.) cross-sectional shaped filaments. Such zoned shaped webs can be formed by, for example, a spunbond die having apertures of differing shapes.

In other embodiments, the relative degree of air permeability of the central zone 32 of the containment member 26 can be controlled by a variety of mechanical deformation techniques that form pores in a substrate or that increase the size of pores or interstices in a substrate or that transform an impermeable substrate into a permeable substrate. Suitable techniques for pore or aperture formation include the use of needle punches, fluid jet streams, laser aperturing, knife or slitting rolls, and other techniques well known in the art. In one embodiment, a laser may be used to selectively aperture a polymeric film that may then become a component of the containment member 26. A polyolefinic film having a basis weight of about 10-30 gsm may be used. Laser aperturing allows for greater precision and replication in aperture formation. The apertured region may then be disposed in the central zone 32 where greater air permeability is desired.

Figure 4A:
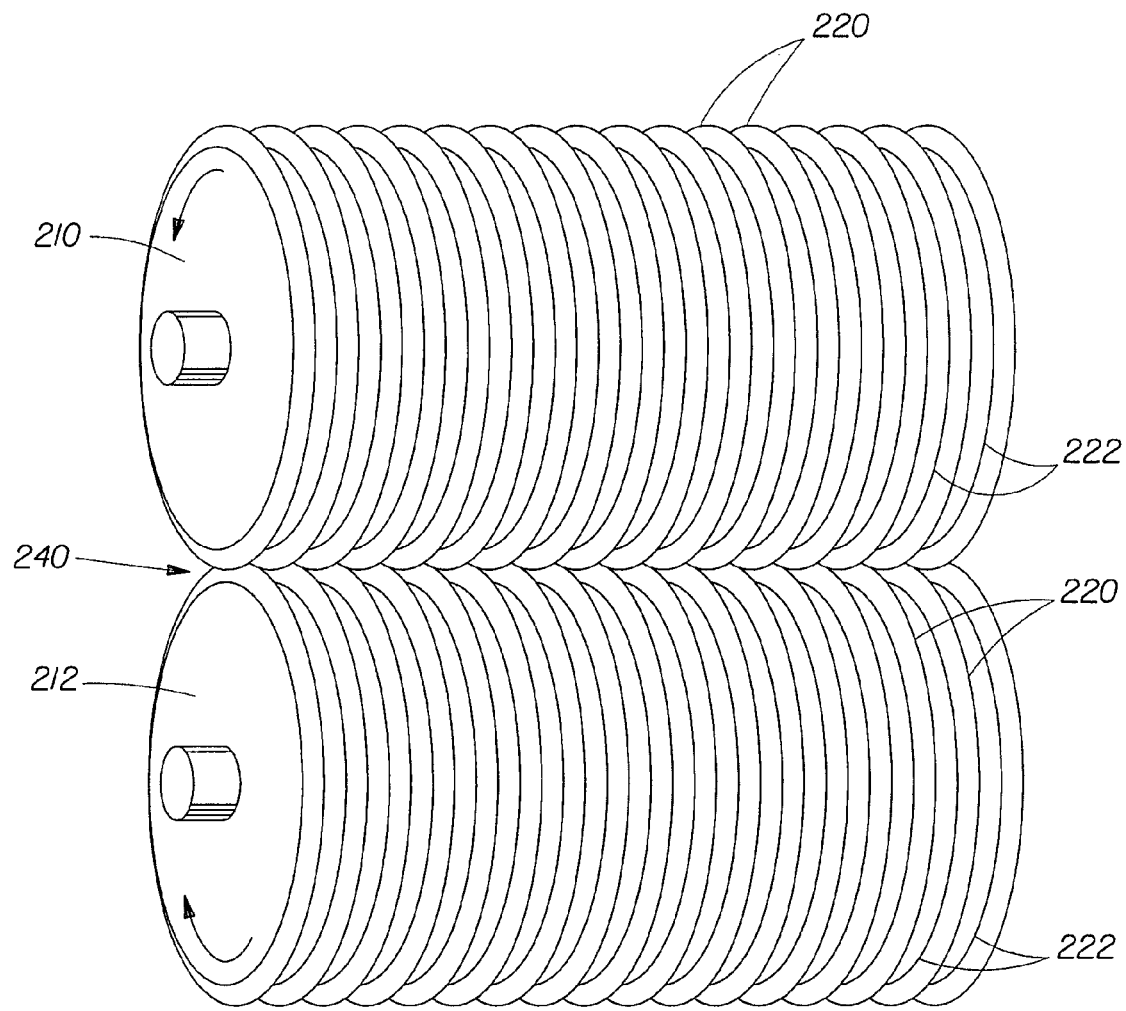
FIG. 4A depicts exemplary forming rolls that may be used to selectively incrementally stretch a containment member.

In other embodiments, the zoned properties of the central zone 32 and the barrier zones 34 may be provided by selective mechanical weakening of the containment member 26. Mechanical weakening may result in pore formation in substrates where pores were not initially present. Mechanical weakening may result in increased pore size or interstices in substrates where pores or interstices were initially present. Mechanical weakening may be performed by stretching or tentering by pulling the web over a laterally curved surface. Alternatively, mechanical weakening may be performed by incrementally stretching one or more portions of the containment member 26. Incremental stretching may be performed by passing a substrate or portions of a substrate through two corrugated interengaging rolls 210, 212 at a nip 240 known as "ring rolling." Exemplary forming rolls 210, 212 are shown in an enlarged perspective view in FIG. 4A. The rolls 210, 212 may include a plurality of axially-spaced, side-by-side, circumferentially-extending, equally-configured teeth 220, respectively, that can be in the form of thin fins of substantially rectangular cross section, or they can have a triangular or an inverted V-shape when viewed in cross section. The outermost tips of the teeth 220 may be rounded to avoid cuts or tears in the substrate that pass between the rolls.

Figure 4B:
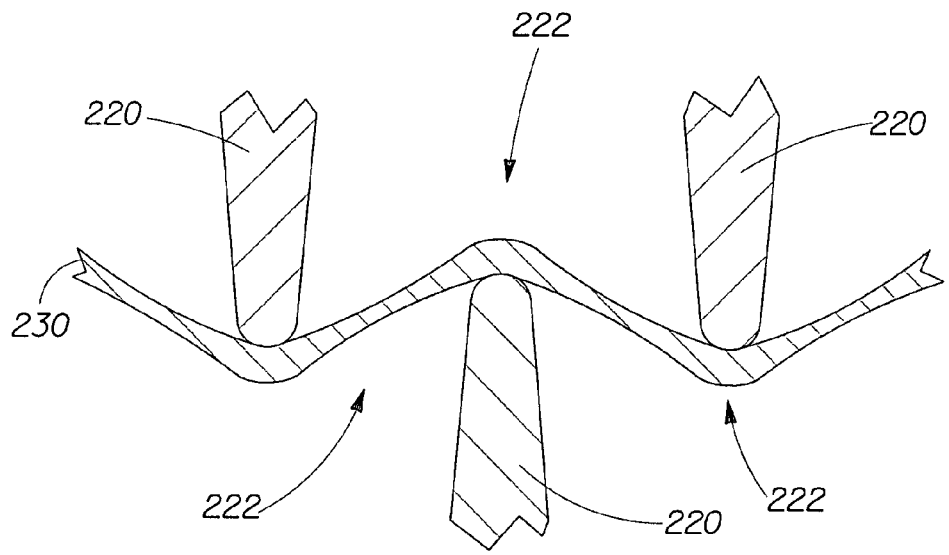
FIG. 4B is an enlarged cross-sectional view of the forming rolls of FIG. 4A with a substrate therebetween.

The spaces between adjacent teeth 220 define recessed, circumferentially-extending, equally configured grooves 222. The grooves 222 can be of any suitable shape so as to accept engagement of the teeth 220. Typically, the shape of the groove is substantially similar to the shape of the teeth 220. FIG. 4B is an enlarged cross-sectional view of interengaged teeth 220 and grooves 222 forming nip 240 with a substrate 230 being modified therebetween. The interengagement of the teeth 220 and grooves 222 of the rolls 210, 212 causes laterally spaced portions of the substrate 230 to be pressed by teeth 220 into opposed grooves 222. In the course of passing between the forming rolls 210, 212, the action of the teeth 220 pressing the substrate 230 into opposing grooves 222 exerts a tensile stresses on the substrate that result in elongation. The tensile stresses cause intermediate portions 232 of the substrate 230 that lie between and span the spaces between the tip portions of adjacent teeth 220 to stretch or extend, which results in a localized reduction of the web thickness. When nonwoven or woven webs are subjected to incremental stretching, individual filaments and/or fibers are detangled, separated, and/or elongated leaving striped areas of lower basis weight.

Incremental stretching is particularly suited for creating zoned properties in the containment member 26 since forming rolls can be configured in a variety of ways such that certain zones of the containment member 26 may experience significant elongation forces while other zones may experience little to no elongation forces. For example, the forming rolls may have interengaging teeth and grooves along only a portion of the total width of the rolls. Such a roll configuration would yield a substrate having an incrementally stretched zone (i.e., the portion of the substrate passed through the teeth and grooves) and one or more zones that are unstretched (i.e., the portions of the substrate not passed through the teeth and grooves). In one embodiment, the containment member 26 may comprise a suitable nonwoven substrate wherein a region of the substrate has been incrementally stretched by 10 to 50% of that region's initial width. This incrementally stretch region may be disposed in the central zone 32 to provide greater air permeability than the non-stretched regions that may form the barrier zones 34.

Further discussion regarding methods for imparting elasticity to an extensible or otherwise substantially inelastic material by using corrugated interengaging rolls which incrementally stretch in the machine and/or cross-machine direction and permanently deform the material is provided in U.S. Pat. Nos. 4,116,892; 4,834,741; 5,143,679; 5,156,793; 5,167,897; 5,422,172; 5,518,801; and 6,383,431. Alternatively, incremental stretching of the printed carrier web 12 may be performed by a pair of interengaging grooved planar plates or other means for incremental stretching (i.e., not rolls) the carrier web 12. Incremental stretching is suitable for a containment member 26 comprising a nonwoven web, woven web, microporous film, or a precursor microporous film (e.g., a polymeric film containing a pore forming agent such as calcium carbonate).

In the embodiments that follow, a relatively air permeable substrate forming the containment member 26 may be treated or modified to improve the liquid impermeability of the barrier zones 34. While the following treatment and modification techniques may be applicable to all substrates, the techniques are particularly applicable to fibrous woven and nonwoven webs. One such method for improving the liquid impermeability of the barrier zones 34 is by applying a chemical treatment that fills in pores and reduce overall pore size distribution or that decrease the surface energy of portions of the containment member 26. Suitable hydrophobic surface treatments are known in the art. Particularly suitable hydrophobic surface treatments include silicone liquids, waxes, and polymers (such as silicone resins, polydimethysiloxanes, crosslinked silicones, silicone liquid elastomers) and fluorinated polymers (such as telomers and polymers containing tetrafluoroethylene and/or perfluorinated alkyl chains). Hydrophobic skin care compositions, such as those disclosed in U.S. Pat. Nos. 5,635,588 and 5,643,588, may also be employed to reduce liquid permeability of the barrier zones. Barrier coatings may be used such as those described in U.S.

Publication No. 2005/0256476A1. Other suitable hydrophobic surface treatments are discussed in U.S. Publication No. 2005/0177123A1. The surface treatments may be selectively applied to the material forming the containment member 26 by conventional means including spraying, slot-coating, immersion, reverse rolls, gravure rolls, and curtain coating.

In other embodiments, the relative liquid permeability of the barrier zones 34 may be altered through the use of high energy surface treatments. Exemplary high energy surface treatments include but are not limited to corona discharge treatment, plasma treatment, UV radiation treatment, ion beam treatment, electron beam treatment, and certain laser treatments including pulsed lasers. The surface energy of select zones of the containment member 26 can lowered (i.e., resulting in increased hydrophobicity) by conducting the high energy surface treatment in an appropriately chosen atmosphere. For example, the barrier zones 34 of the containment member 26 may be subjected to plasma treatment in a methane atmosphere. Such treatment is particularly effective when the containment member 26 comprises a substantially hydrophilic substrate such as a woven or nonwoven including cellulosic fibers.

In other embodiments, the relative liquid permeability of the barrier zones 34 may be altered through the use of barrier coatings. Particularly for porous substrates such as woven and nonwoven webs, a coating may be applied that serves as an impediment to liquid penetration. The barrier zones 34 of the containment member 26 may be coated with wax, an adhesive, or a composition that is capable of forming a liquid impermeable film. Suitable barrier coatings and techniques are further described in U.S. Publication Nos. 2003/0065298A1 and 2002/0035354A1 as barrier structures.

In other embodiments, the relative liquid permeability of the barrier zones 34 may be altered by physically deforming the containment member 26 to reduce or eliminate pores. For example, a polymeric nonwoven such as a polyolefin spunbond web may be of subjected to compression and/or heat. The nonwoven may be compressed so as to consolidate the constituent fibers or filaments thereby reducing the pore size. The nonwoven may be heated to a point where the polymer fibers or filaments are softened. Individual fibers or filaments may meld together thereby reducing pore size. Both heating and compression may be applied such as by subjecting the containment member 26 to a heated nip. It should be recognized that compression and heating may also be effective in improving the water impermeability of other materials such a microporous films. For example, a nonwoven web such as a spunbond or carded web may be selectively subjected to an engraved calendar roll which results in localized bonds where the fibers have been fused together. By increasing the number and/or area of the bonds within a region, the air permeability of that region may diminish while the liquid impermeability may be improved. A nonwoven web with varying bond area and/or number may be a component of the containment member 26 such that the region having a greater bond area and/or number is disposed in the barrier zone 34.

Figure 5:
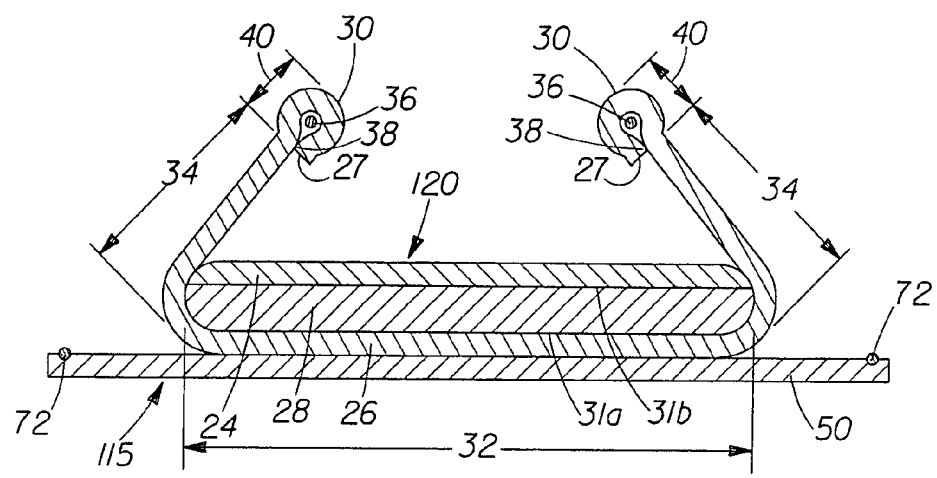
FIG. 5 is a cross-sectional view, taken along the lateral centerline, of the diaper of FIG. 1 showing a central zone, barrier zones, and bonding zones.

It may be desirable for the containment member 26 to contain more than two zones exhibiting distinctly different physical characteristics. FIG. 5 is a cross sectional view of an absorbent assembly 22 taken along a lateral centerline. The absorbent assembly 22 of FIG. 5 is substantially similar to that shown in FIG. 2A; however, the containment member 26 is shown to have three zones: a central zone 32, barrier zones 34, and bond zones 40. The bond zone 40 is the portion of the containment member 26 utilized in the attachment or joining of the elastic member 36. In some embodiments, the bond zone 40 may be defined as the portion of the containment member 26 to which the elastic member 36 is joined. In other embodiments, such as the one shown in FIG. 5, the bond zone 40 encompasses the portion of the containment member 26 that is folded over and bonded to itself. In this embodiment, the bond zone 40 extends from the upstanding edge 30 to the inboard edge of the bond site 38. However, in other embodiments, the bond zone 40 is delineated by a change in containment member 26 characteristics from the barrier zone 34 and/or the central zone 32.

Figure 6:
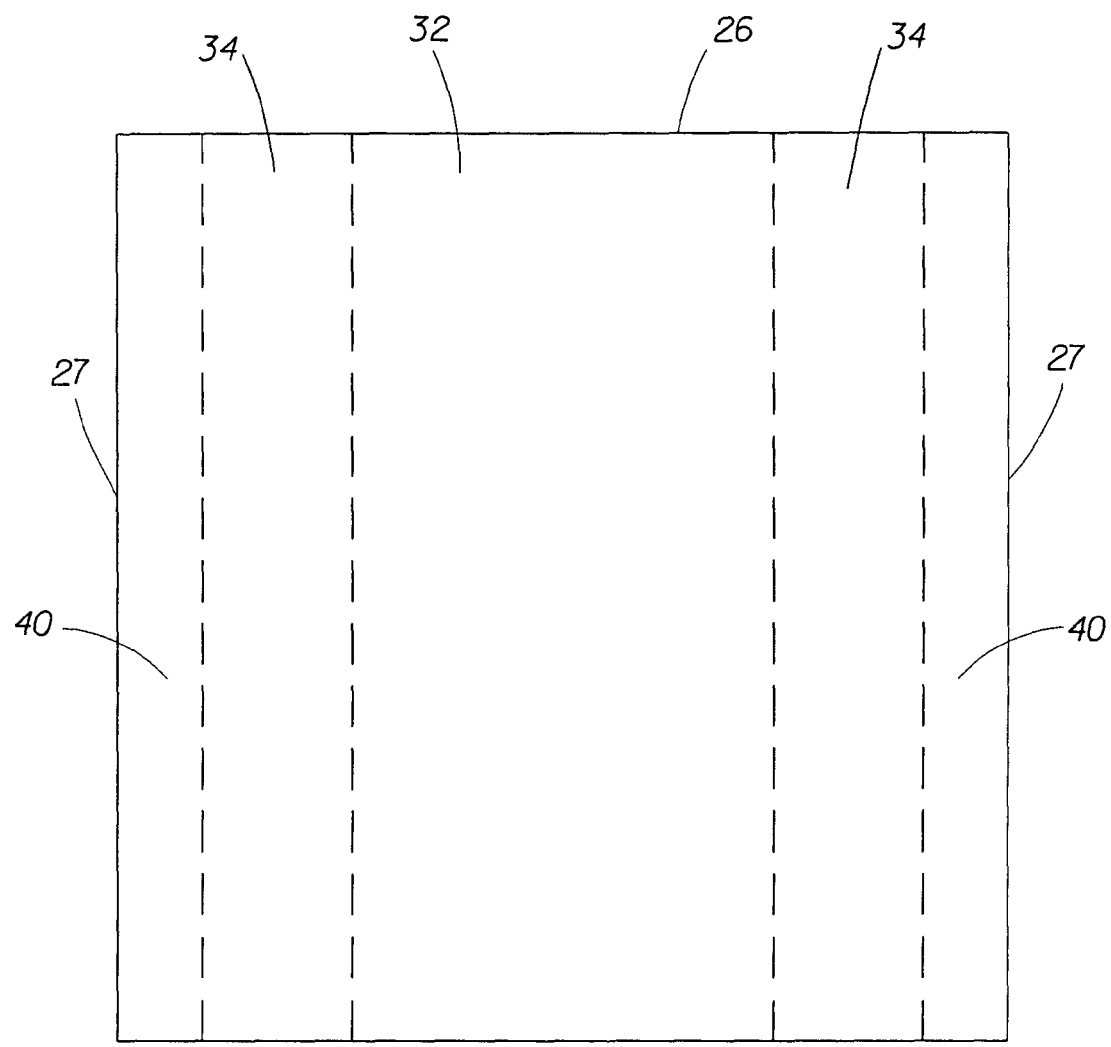
FIG. 6 is a plan view of a containment member such as provided in FIG. 5 absent other structures prior to being incorporated in a diaper.

FIG. 6 depicts a plan view of a containment member 26 without the elastic member 36 and prior to being incorporated into the absorbent assembly 22 as shown in FIG. 5. The containment member 26 is shown having the central zone 32, two barrier zones 34 laterally outboard of the central zone 32, and two bond zones 40 laterally outboard of the barrier zones 34. The dotted lines represent the approximate boundary between the central zone 32 and the barrier zones 34 and between the barrier zones 34 and the bond zones 40. While this embodiment depicts the boundary between the central zone 32, the barrier zones 34, and bond zones 40 as being linear, the boundary should not be limited straight lines. The boundary may be curvilinear or composed of connecting line segments.

The bond zone 40 may have characteristics different from those of the central zone 32 and/or the barrier zones 34. Internal surfaces of the bond zone 40 may be coated with adhesive which serves to form the bond site 38 and/or the attachment of the elastic member 36 directly to the containment member 26. Therefore, it may be desirable that the bond zone 40 have improved resistance to adhesive bleed through (adhesive penetrating pores or interstices in the containment member 26).

Typically, during manufacture, molten adhesive is applied to a portion of the containment member 26. The adhesive bearing portion of the containment member 26 may be folded over an elastic member 36 such as is shown in FIG. 5. The bond site 38 may be subjected to a nip roll or other pressure inducing mechanism which aids the adhesive interconnection. However, the nip roll may exert a pressure that can push the adhesive through the pores or interstices of the containment member 26. This is commonly referred to as "bleedthrough" and is undesirable. One way to reduce adhesive bleed through is by reducing the pore size or volume of the interstices in the containment member 26. Several methods for varying pore size have been discussed above in regard to the central zone 32 and the barrier zones 34; these methods are equally applicable to varying the pore size or interstitial volume of the bond zone 40.

In certain embodiments, the central zone 32 may have a greater air flow than the barrier zone 34 and the barrier zone 34 has a greater air flow than the bond zone 40. In other embodiments, the air permeability of the central zone 32 is about 10% greater than that of the barrier zone 34 and the air permeability of the barrier zone 34 is about 10% greater than that of the bond zone 40. Additionally, the bond zone 40 may have a greater hydrohead than the barrier zone 34 and/or the central zoned 32.

Furthermore, any treatment or modification applied to the bond zone 40 should not adversely impact the function of the adhesive. As a result, hydrophobic surface treatments and barrier coatings such as waxes or film formers may present on the adjacent barrier zone 34 but may, in some instances, be disfavored on the bond zone 40.

Returning to the construction of the absorbent assembly 22, other optional structures may be present in the absorbent assembly. FIG. 7A-D illustrate embodiments of the absorbent assembly further comprising an impermeable member 55.

The impermeable member 55 may be any suitable substrate that is substantially liquid impermeable by itself or, in a situation where the impermeable member 55 is joined to another substrate, that renders the resulting laminate substantially liquid impermeable. Ideally, the impermeable member 55 will exhibit air and/or vapor permeability. Suitable materials for use as the impermeable member 55 include woven webs, nonwoven webs, polymeric films, microporous films, and composites and laminates thereof. The impermeable member 55 may be joined to the absorbent assembly by any conventional bonding technique such as by an adhesive, pressure bonds, or heat bonds.

In certain embodiments it is desirable that the overall size of the impermeable member 55 be minimized. Even in executions where the impermeable member 55 is air and/or vapor permeable, the liquid impermeability of the member 55 generally limits the amount of air and/or vapor permeability that can be exhibited. Therefore, to achieve maximum air and/or vapor permeability the size of the impermeable member 55 may be minimized. In certain embodiments, the impermeable member 55 is within the central zone 32 (i.e., impermeable member 55 does not extend beyond the central zone 32). In other embodiments, the impermeable member 55 is bounded by the upstanding edge 30 or terminal edge 27, as shown in FIG. 5. In other embodiments, the impermeable member 55 is coterminous with the containment member 26 or is bounded by the containment member 26 (i.e., does not extend beyond the terminal edges 27 of the containment member 26 in a plan view such as shown in FIG. 3).

Figure 7A:
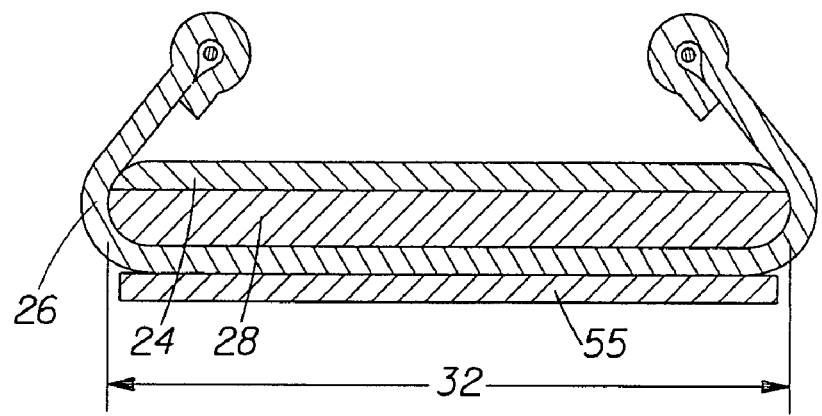
FIGS. 7A-D are cross-sectional views of an absorbent assembly further comprising an impermeable member.
Figure 7B:
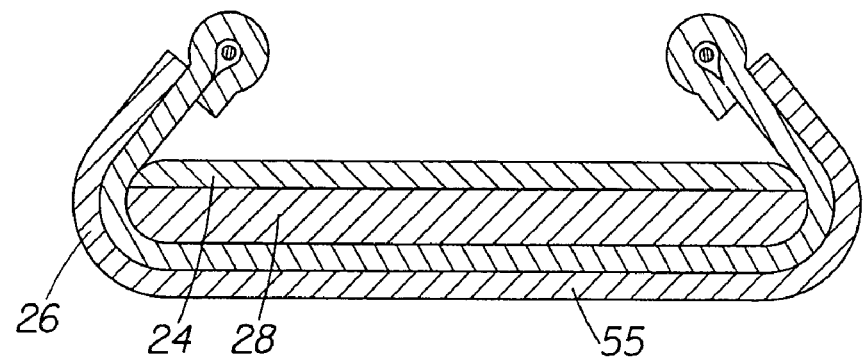
Figure 7C:
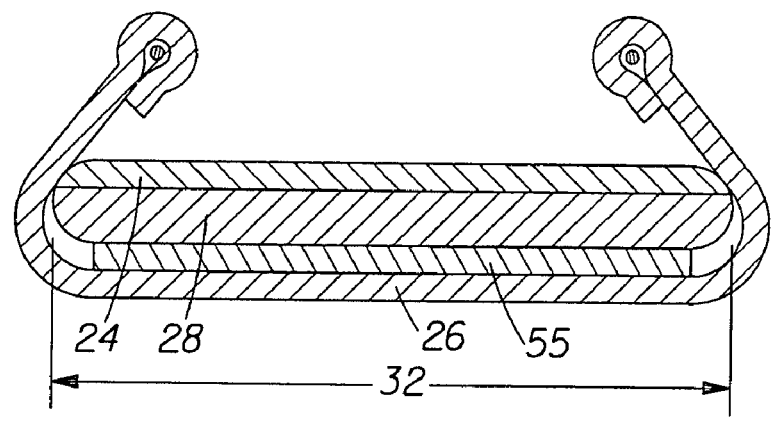
Figure 7D:
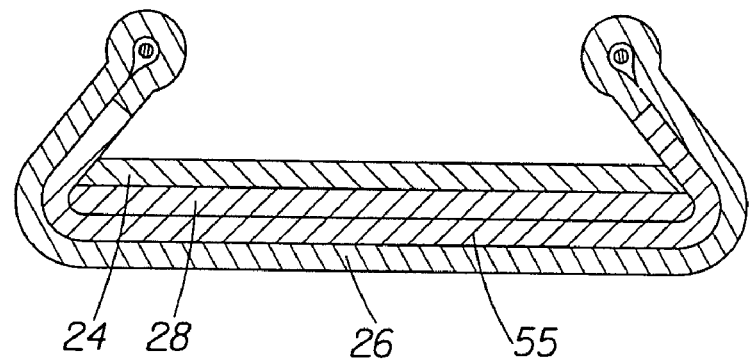

FIGS. 7A-B depict absorbent assemblies having the impermeable member 55 disposed adjacent the garment-facing surface of the containment member 26. In FIG. 7A, the impermeable member 55 is laterally bounded within the central zone 32. In FIG. 7B, the impermeable member 55 is laterally bounded by the containment member 26. FIGS. 7C-D depict absorbent assemblies having the impermeable member 55 disposed between the containment member 26 and the absorbent core 28. In FIG. 7C, the impermeable member 55 is laterally bounded within the central zone 32. In FIG. 7D, the impermeable member 55 is laterally bounded by the containment member 26.

Test Methods
Air Permeability

Air permeability is determined by measuring the time in which a standard volume of air is drawn through a test specimen of a defined area at a constant pressure and temperature. This test is particularly suited to materials having relatively high permeability to gases, such as nonwovens, apertured films and the like. The air permeability test is performed according to ASTM D737-96 entitled "Standard Test Method for Air Permeability of Textile Fabrics" with the following test parameters. A TexTest FX3300 instrument is used. (Available by Textest AG in Switzerland (www.textest.ch), or from Advanced Testing Instruments in Spartanburg S.C., USA.) The test is conducted in a laboratory environment at about 22±2° C. and about 50% relative humidity. The test pressure drop is 125 Pascal and the test area is 38 cm$^2$. In this test, the instrument creates a constant differential pressure across the sample which draws air through the sample. The rate of air flow through the sample is measured in ft$^3$/ft$^2$/min (often called cfm or ft/min) or m$^3$/m$^2$/min (or m/min). For each sample, three replicates should be run, and the average result is reported.

Hydrostatic Head (Hydrohead) Pressure

The property determined by this test is a measure of the liquid barrier property (or liquid impermeability) of a material. Specifically, this test measures the hydrostatic pressure the material will support: when a controlled level of water penetration occurs. The hydrohead test is performed according to EDANA 120.2-02 entitled "Repellency: Hydrostatic Head" with the following test parameters. A TexTest Hydrostatic Head Tester FX3000 (available from Advanced Testing Instruments, Corp., Spartanburg, S.C., or by Textest AG in Switzerland (www.textest.ch)) is used. For this test, pressure is applied to a defined sample portion and gradually increases until water penetrates through the sample. The test is conducted in a laboratory environment at about 22±2° C. temperature and about 50% relative humidity. The sample is clamped over the top of the column fixture, using an appropriate gasketing material (o-ring style) to prevent side leakage during testing. The area of water contact with the sample is equal to the cross sectional area of the water column, which equals 28 cm$^2$. Water is pumped into the water column at a rate of 20 mbar/min. Thus, the sample is subjected to a steadily increasing water pressure on one surface. When water penetration appears in three locations on the other surface of the sample, the pressure (measured in mbar) at which the third penetration occurs is recorded. If water immediately penetrates the sample (i.e., the sample provided no resistance), a zero reading is recorded. For each material, three specimens are tested and the average result is reported.

Basis Weight

Basis weight can be measured consistent with compendial methods EDANA ERT-40.3-90 entitled "Mass per Unit Area" with the test parameters that follow. Basis weight is defined as mass per unit area, with grams per square meter (often called gsm rather than g/m$^2$) as the preferred unit. Required instruments are a scissors or a die-cutter for sample cutting and an accurate weighing device (scale). A sample is cut to a total area of 100 cm$^2$ per layer with an accuracy and precision of ±0.5%. A scale or balance is needed with 0.001 g sensitivity, readable, calibrated and accurate to within 0.25% of the applied load. The samples are conditioned at 23° C. (±2° C.) and at a relative humidity of about 50% for 2 hours to reach equilibrium. Weigh the cut sample with 10 plies from the sample area for a total of 1000 cm$^2$=0.1 m$^2$ on an analytical balance to the nearest 0.001 g and record the weight. (For samples thicker than 1 mm, weighing only 1 ply is preferred but should be noted if done so.) Calculate the basis weight by dividing the weight by the sample area (all layers tested) to give the basis weight in gsm. All data are recorded for statistic analysis.

Fiber Diameter (and Denier)

Fiber diameters are determined by using a Scanning Electron Microscope (SEM) and image analysis software. A magnification of 500 to 10,000 is chosen such that the fibers (or filaments) are suitably enlarged for measurements. Image analysis software for automatic sampling of fiber diameter in the SEM picture is possible, but also a more manual procedure can be used. In principle the edge of a randomly selected fiber is sought and then measured across the width (perpendicular to fiber direction at that spot) to the other edge of the fiber. A scaled and calibrated image analysis tool provides the scaling to get the actual reading in meter or mm or micrometers (μm), e.g. Several fibers or filaments are thus randomly selected across the sample of web in the SEM. Typically several samples from a web are cut and tested in this manner. Altogether at least about 100 such measurements are made and all data are recorded for statistic analysis. If the result is to be recorded in denier, then the following calculation needs to be made. Diameter in denier=Cross-sectional area×density×9000 m×1000 g/kg. The cross-sectional area is π×diameter$^2$/4. The density for PP, e.g., can be taken as 910 kg/m$^3$. To obtain decitex (dtex), instead of using 9000 m, use 10,000 m.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm".

All documents cited in the Detailed Description of the Invention are, in relevant part, incorporated herein by reference; the citation of any document is not to be construed as an admission that it is prior art with respect to the present invention. To the extent that any definition or meaning of a term in this written document conflicts with any definition or meaning of the term in a document incorporated by reference, the definition or meaning assigned to the term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm".

What is claimed is:

1. An absorbent article comprising a garment body and an absorbent assembly joined to the garment body such that the absorbent assembly is disposed between the garment body and a wearer during wear, wherein said absorbent assembly has a garment-facing surface and a body-facing surface, wherein said absorbent assembly comprises:
   a) a liquid permeable topsheet,
   b) a containment member joined to the topsheet, and
   c) an absorbent core disposed between said containment member and said topsheet, said absorbent core having opposing longitudinal core edges;
   wherein the containment member is formed of a continuous substrate and comprises:
      i) respective opposing longitudinal containment member edges and a pair of elastic members respectively joined proximate to the containment member edges;
      ii) a central zone disposed between the absorbent core and the garment body; and
      iii) a pair of barrier zones respectively disposed at either longitudinal side of the central zone, between the central zone and the opposing containment member edges, the barrier zones and the containment member edges forming respective upstanding longitudinal barrier cuffs, and
      wherein the central zone has a greater air flow according to the Air Permeability Test than the barrier zones and the barrier zones have a greater hydrohead according to the Hydrostatic Head Pressure Test than the central zone; and the central zone has an air flow of at least about 100 m$^3$/m$^2$/min at a pressure drop of 125 Pa.

2. The absorbent article of claim 1 wherein the central zone has an air flow, according to the Air Permeability Test, about 10% greater than that of the barrier zones.

3. The absorbent article of claim 1 wherein the containment member comprises a substrate having first pores in the central zone having a first average pore size and second pores in the barrier zones having a second average pore size, wherein the first average pore size is about 20% greater than the second average pore size.

4. The absorbent article of claim 3 wherein the barrier zones of the containment member have been heated, compressed, or both to reduce the size of the second pores.

5. The absorbent article of claim 1 wherein the containment member comprises a substrate having a basis weight in the central zone less than the basis weight in the barrier zones.

6. The absorbent article of claim 1 wherein the containment member comprises a fibrous nonwoven.

7. The absorbent article of claim 6 wherein the fibrous nonwoven comprises first fibers in the central zone and second fibers in the barrier zones; wherein the first fibers predominately have a first cross-sectional shape, wherein the second fibers predominately have a second cross-sectional shape, and wherein the first cross-sectional shape is different from the second cross-sectional shape.

8. The absorbent article of claim 6 wherein the fibrous nonwoven comprises first fibers in the central zone having a first denier and second fibers in the barrier zones having a second denier; wherein the first denier is different from the second denier.

9. The absorbent article of claim 6 wherein a secondary substrate is joined to the fibrous nonwoven such that the secondary substrate is substantially disposed in the barrier zones.

10. The absorbent article of claim 9 wherein the secondary substrate is liquid impermeable.

11. The absorbent article of claim 6 wherein the nonwoven comprises fine fibers in the barrier zones and, optionally, in the central zone such that the barrier zones comprise a greater basis weight of fine, fibers than does the central zone.

12. The absorbent article of claim 1 wherein the central zone of the containment member is mechanically treated to increase air permeability, wherein the mechanical treatment is selected from a group consisting of perforating, laser aperturing, fluid jet aperturing, incremental stretching, ring rolling, tentering, general stretching or combinations thereof.

13. The absorbent article of claim 1 wherein the barrier zones are coated with a hydrophobic surface. coating or a barrier coating and wherein the central zone is substantially free of the hydrophobic surface coating or harrier coating.

14. The absorbent article of claim 1 wherein the barrier zones exhibit a lower surface energy than does the central zone.

15. The absorbent article of claim 1 wherein the absorbent article further comprises an impermeable member disposed between the absorbent assembly and the garment body.

16. The absorbent article of claim 1 wherein the absorbent assembly further comprises an impermeable member disposed between containment member and the absorbent core.

17. The absorbent article of claim 1 wherein the garment body consists essentially of a liquid permeable substrate.

18. The absorbent article of claim 1 wherein the containment member comprises a composite substrate or laminate substrate.

19. An absorbent article comprising a garment body and an absorbent assembly joined to the garment body such that the absorbent assembly is disposed between the garment body and a wearer during wear, wherein said absorbent assembly has a garment-facing surface and a body-facing surface, wherein said absorbent assembly comprises:
   a) a liquid permeable topsheet,
   b) a containment member joined to the topsheet, c) an absorbent core disposed between said containment member and said topsheet, said absorbent core having opposing longitudinal core edges;

wherein the containment member is formed of a continuous substrate and comprises:
  i) respective opposing longitudinal containment member edges and a pair of elastic members respectively joined proximate to the containment member edges;
  ii) a central zone disposed between the absorbent core and the garment body; and
  iii) a pair of bond zones respectively disposed adjacent to the elastic members, and
  iv) a pair of barrier zones respectively disposed at either longitudinal side of the central zone, between the central zone and the opposing containment member edges, the barrier zones and the containment member edges forming respective upstanding longitudinal barrier cuffs:

wherein the central zone has a greater air flow according to the Air Permeability Test than the barrier zones; wherein the bond zones have a greater hydrohead according to the Hydrostatic Head Pressure Test than the barrier zones; and the central zone has an air flow of at least about 100 m$^3$/m$^2$/min at a pressure drop of 125 Pa.

20. An absorbent article comprising a garment body and an absorbent assembly joined to the garment body such that the absorbent assembly is disposed between the garment body and a wearer during wear, wherein the garment body consists essentially of a liquid permeable material, wherein said absorbent assembly has a garment-facing surface and a body-facing surface, wherein said absorbent assembly comprises:
  a) a liquid permeable topsheet,
  b) a containment member, and
  c) an absorbent core disposed between said containment member and said topsheet, said absorbent core having opposing longitudinal core edges;

wherein the containment member is formed of a continuous substrate and comprises:
  i) respective opposing longitudinal containment member edges and a pair of elastic members respectively joined proximate to the containment member edges;
  ii) a central zone disposed between the absorbent core and the garment body,
  iii) a pair of barrier zones respectively disposed at either longitudinal side of the central zone, between the central zone and the opposing containment member edges, the barrier zones and the containment member edges forming respective upstanding longitudinal barrier cuffs, and wherein the central zone has a greater air permeability than the barrier zones and the barrier zones have a greater hydrohead than the central zone; and the central zone has an air flow of at least about 100 m$^3$/m$^2$/min at a pressure drop of 125 Pa.

* * * * *